United States Patent
Chen (10) Patent No.: US 9,625,726 B2
(45) Date of Patent: Apr. 18, 2017

(54) LENS ARRAY-BASED ILLUMINATION FOR WAFER INSPECTION

(71) Applicant: KLA-Tencor Corporation, Milpitas, CA (US)

(72) Inventor: Qibiao Chen, Fremont, CA (US)

(73) Assignee: KLA-Tencor Corp., Milpitas, CA (US)

( * ) Notice: Subject to any disclaimer, the term of this patent is extended or adjusted under 35 U.S.C. 154(b) by 22 days.

(21) Appl. No.: 14/871,943

(22) Filed: Sep. 30, 2015

(65) Prior Publication Data

US 2016/0161749 A1   Jun. 9, 2016

Related U.S. Application Data

(60) Provisional application No. 62/088,305, filed on Dec. 5, 2014.

(51) Int. Cl.
| | |
|---|---|
| *G01N 21/00* | (2006.01) |
| *G02B 27/09* | (2006.01) |
| *G01N 21/47* | (2006.01) |
| *G01N 21/95* | (2006.01) |
| *G02B 13/14* | (2006.01) |
| *G01N 21/88* | (2006.01) |

(52) U.S. Cl.
CPC ..... *G02B 27/0927* (2013.01); *G01N 21/4738* (2013.01); *G01N 21/8806* (2013.01); *G01N 21/9501* (2013.01); *G02B 13/143* (2013.01); *G02B 27/0961* (2013.01); *G01N 2021/8822* (2013.01); *G01N 2201/0631* (2013.01); *G01N 2201/0638* (2013.01)

(58) Field of Classification Search
CPC .............. G02B 27/0927; G02B 13/143; G02B 27/0961; G01N 21/9501; G01N 21/4738
USPC ................... 356/237.2–237.6, 445, 326, 394
See application file for complete search history.

(56) References Cited

U.S. PATENT DOCUMENTS

| | | | |
|---|---|---|---|
| 6,927,847 B2* | 8/2005 | Yoshida | G01N 21/95684 356/237.4 |
| 7,460,248 B2* | 12/2008 | Kurtz | A61B 5/0059 356/495 |

(Continued)

FOREIGN PATENT DOCUMENTS

| | | |
|---|---|---|
| JP | 2001-165869 | 6/2001 |
| JP | 2006-064380 | 3/2006 |

OTHER PUBLICATIONS

International Search Report for PCT/US2015/064093 mailed Feb. 29, 2016.

*Primary Examiner* — Tanifur R. Chowdhury
*Assistant Examiner* — Isiaka Akanbi
(74) *Attorney, Agent, or Firm* — Ann Marie Mewherter (57) ABSTRACT

Systems configured to provide illumination for wafer inspection performed by a wafer inspection tool are provided. One system includes one or more pupil lenses configured to focus a first far field pattern having a shape different than a shape of light generated by a light source. The system also includes a field lens array positioned between the one or more pupil lenses and an aperture stop. In addition, the system includes a lens group configured to focus a second far field pattern generated by the field lens array to a back focal plane of the lens group. The back focal plane of the lens group is a field plane of a wafer inspection tool at which a wafer to be inspected is placed during wafer inspection.

26 Claims, 3 Drawing Sheets

(56) References Cited

U.S. PATENT DOCUMENTS

| | | | |
|---|---|---|---|
| 2002/0015158 A1* | 2/2002 | Shiode | G03F 9/7026 356/614 |
| 2004/0125459 A1* | 7/2004 | Tanitsu | G02B 3/0056 359/619 |
| 2006/0055834 A1* | 3/2006 | Tanitsu | G03B 27/42 349/5 |
| 2006/0164649 A1 | 7/2006 | Rosengaus | |
| 2007/0258077 A1* | 11/2007 | Tanaka | G02B 27/0905 355/71 |
| 2008/0074632 A1* | 3/2008 | Tanitsu | G03B 27/42 355/71 |
| 2008/0273196 A1 | 11/2008 | Fairley et al. | |
| 2009/0225412 A1* | 9/2009 | Mochida | G02B 27/0961 359/385 |
| 2014/0132952 A1 | 5/2014 | Zhu et al. | |
| 2014/0347645 A1* | 11/2014 | Tanitsu | G03F 7/70108 355/67 |

* cited by examiner

LENS ARRAY-BASED ILLUMINATION FOR WAFER INSPECTION

BACKGROUND OF THE INVENTION

1. Field of the Invention

This invention generally relates to systems configured for lens array-based illumination for wafer inspection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail (killer defect size also shrinks with the device size).

Uniform illumination fields for wafer inspection are typically generated via one of the following methods. For example, a uniform illumination field may be generated by one or more solid rectangular rods via total internal reflection from the sides of the rods for broad band electromagnetic spectra. In another example, a uniform illumination field may be generated by a single hollow light pipe with a relatively high reflective coating for narrow band electromagnetic spectra, typically at wavelengths less than 260 nm, where material absorption and optical damage become significant for optical materials. In an additional example, a uniform illumination field may be generated by diffractive optics with relay optics for narrow band electromagnetic spectra.

Illumination pupils (not necessarily top hat uniform pupil) for wafer inspection are typically generated via the following methods. For example, an illumination pupil may be generated by diffractive optics with relay optics for narrow band electromagnetic spectra. In another example, an illumination pupil may be generated with refractive condenser optics for wider band electromagnetic spectra. In an additional example, an illumination pupil may be generated with reflective optics, especially ellipsoidal optics for broadband electromagnetic spectra.

For wafer inspection, the following combinations are used to generate combined field and pupil. For narrow band, diffractive optics and refractive optics, for example, an aspherical lens with relay optics may be used to generate a pupil with a desired shape and non-uniformity followed by diffractive optics with relay optics to generate one or more rectangular uniform fields for narrow band electromagnetic spectra. For broad band, the combined field and pupil may be generated by a combination of refractive condenser optics and light pipe (solid or hollow) to form a uniform pupil and field. In another example for broad band, the combined field and pupil may be generated by an ellipsoidal reflector followed by a light pipe to form a pupil and uniform field. In an additional example for broad band, the combined field and pupil may be generated by an ellipsoidal reflector followed by light pipe, relay optics, and light pipe to form uniform pupil and field. In a further example for broad band, the combined field and pupil may be generated by an ellipsoidal reflector followed by a light pipe, micro lens array, and light pipe to form a uniform pupil and field.

There are, however, a number of disadvantages to the currently used optical configurations described above. For example, diffractive optics are in general for narrow band applications and are not suitable for broad band applications due to material dispersion. In addition, the refractive condenser plus light pipe combination has a limited light collection solid angle, e.g., $\sim\pi$ due to the condenser numerical aperture (NA, e.g., NA<=0.9), as plasma sources are in general emitting in $4\pi$ solid angle. The working distance of the condenser may be too short to be used with a relatively high power laser induced plasma source. In another example, the collection solid angle of an ellipsoidal reflector can approach $3\pi$. (The collection solid angle can, in theory, approach nearly $4\pi$ with two ellipsoidal mirrors, where a spherical mirror is considered a special ellipsoidal mirror. However, such a configuration is difficult to implement and the potential light gain may be limited due to plasma re-absorption.) However, the angular magnification of the ellipsoidal reflector with reasonable working distance can be substantially high such that the pupil generated by the ellipsoidal reflector alone will have substantially large non-uniformity. This non-uniformity is undesirable for machine-to-machine matching. In a further example, the rod plus relay optics (or lens array) plus rod approach for relatively high power, broad band deep ultraviolet (DUV) applications is in general undesirable due to thermal management, material handling, and material absorption and life time concerns.

Accordingly, it would be advantageous to develop systems for providing illumination for wafer inspection that do not have one or more of the disadvantages described above.

SUMMARY OF THE INVENTION

The following description of various embodiments is not o be construed in any way as limiting the subject matter of the appended claims.

One embodiment relates to a system configured to provide illumination for wafer inspection performed by a wafer inspection tool. The system includes a light source configured to generate light. The system also includes one or more pupil lenses configured to generate a first far field pattern of the light having a shape different than a shape of the light generated by the light source. In addition, the system includes a field lens array positioned between the one or more pupil lenses and an aperture stop positioned proximate to the field lens array. The field lens array is configured to generate a second far field pattern of the light having a cross-sectional shape that is substantially the same as a cross-sectional shape of each individual lens in the field lens array. The system further includes a lens group. The aperture stop is placed between the field lens array and the lens group. The lens group is configured to focus the second far field pattern to a back focal plane of the lens group. The back focal plane of the lens group is a field plane of a wafer inspection tool at which a wafer to be inspected is placed during wafer inspection such that the wafer is illuminated with the second far field pattern. The system may be further configured as described herein.

Another embodiment relates to a system configured to inspect a wafer. The system includes all of the elements of the system described above. In addition, this system includes one or more detectors configured to detect light from the wafer due to illumination of the wafer with the second far field pattern focused by the lens group to the field plane and to generate output responsive to the detected light. This system also includes a computer subsystem configured to detect defects on the wafer based on the output. The system may be further configured as described herein.

BRIEF DESCRIPTION OF THE DRAWINGS

Other Objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to all lens array illumination systems. In other words, the embodiments described herein include lens arrays that are configured to generate the illumination pupil and illumination field for the system, One embodiment relates to a system configured to provide illumination for wafer inspection performed by a wafer inspection tool. For wafer inspection, it is important to have substantially uniform pupil illumination and substantially consistent illumination field profiles from tool-to-tool. In addition, for shorter wavelengths, it is important to have an optical configuration that can sustain relatively high fluence for longer lifetimes.

The embodiments described herein are configured for providing such capability by providing a system that may produce one or more of the following: illumination light with a broad band electromagnetic spectrum; spatially uniform illumination for the wafer; consistent angularly uniform (or controlled angular distribution) illumination for all locations of the wafer; and an illumination architecture with key components that enable an extended life time at a reasonable cost of ownership under the relative high power density of deep ultraviolet (DUV) and vacuum ultraviolet (VUV) electromagnetic spectra. Consistent angularly uniform illumination in the context of the embodiments described herein means that the incident energy to the wafer from all angles (within the limitations of the system) is uniform or substantially uniform. It also means that the irradiance at the illumination pupil is uniform or substantially uniform.

Figure 1:
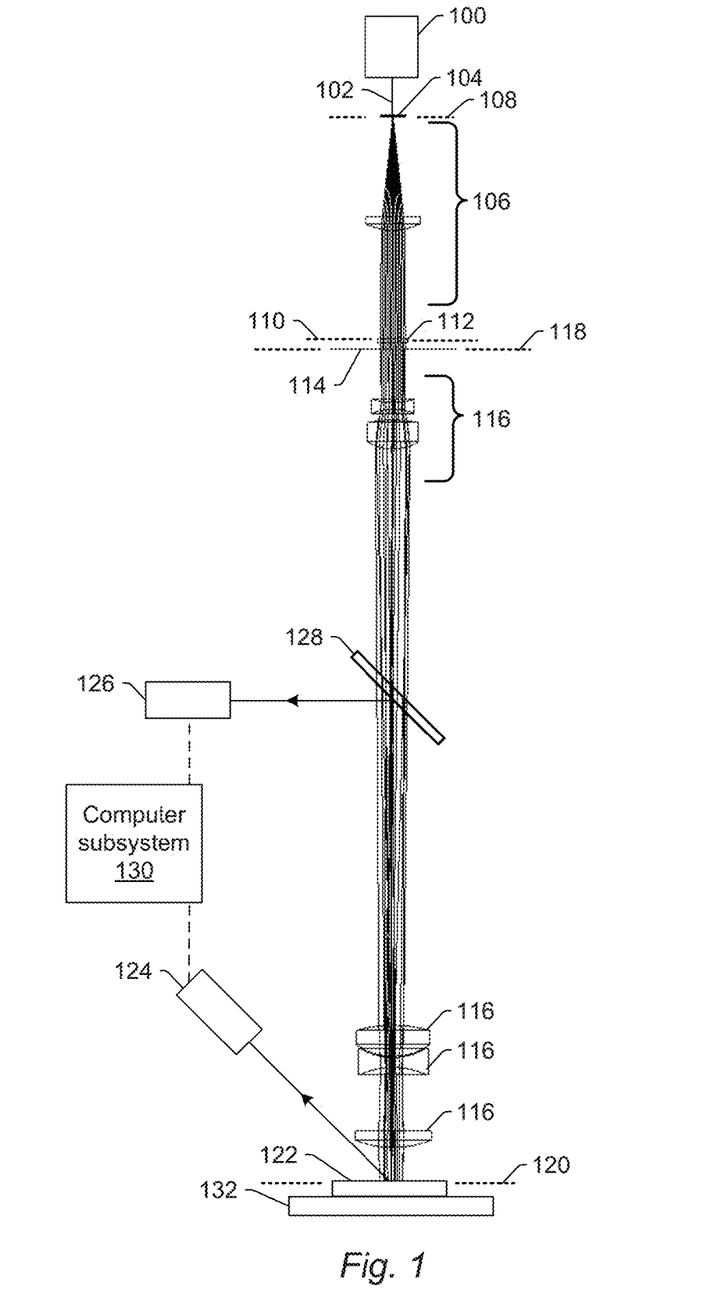
FIG. 1 is a schematic diagram illustrating a side view of embodiments of systems configured as described herein.

FIG. 1 illustrates one embodiment of a system configured to provide illumination for wafer inspection performed by a wafer inspection tool. The system includes light source 100 configured to generate light 102. In one embodiment, the light generated by the light source is broad band light. For example, light source may be a broad band plasma light source. Broad band light can be generally defined as light having non-discrete wavelengths spanning a relatively large range of wavelengths. In another embodiment, the light generated by the light source includes DUV light. DUV light can be generally defined as light having a wavelength or wavelengths between about 200 nm and about 400 nm. In an additional embodiment, the light generated by the light source includes VUV light. VUV light can be generally defined as light having a wavelength or wavelengths below about 200 nm. The light source and the wavelength(s) of the light generated by the light source and used by the embodiments described herein may vary depending on, for example, the type of wafer inspection to be performed with the illumination and/or the type of wafer that is to be inspected using the illumination. In principle, there is no limit on the wavelength(s) that the embodiments described herein can be used for, as long as there is material with which the lens arrays can be fabricated that has sufficient transmission of the light.

The system also includes one or more pupil lenses 104 positioned in the path of light 102 from the light source. The one or more pupil lenses are configured to generate a first far field pattern of the light having a shape different than a shape of the light generated by the light source.

In one embodiment, the one or more pupil lenses include a pupil lens array, and the shape that the first far field pattern has is a cross-sectional shape of the first far field pattern that is substantially the same as a cross-sectional shape of each individual lens in the pupil lens array. A "cross-sectional shape" as that term is used herein with respect to a far field pattern is a shape of the far field pattern in a plane parallel to the plane to which the far field pattern is focused. A "cross-sectional shape" as that term is used herein with respect to an individual lens is a shape of the individual lens in a plane that is perpendicular to the direction of light travel through the individual lens (or the optical axis of the lens).

In one such embodiment, the cross-sectional shape of the first far field pattern of the light is hexagonal. For example, the far field pattern of the pupil lens array may be substantially the same as the pupil lens array's unit cell shape, which may be hexagonal. In addition, since the individual lenses of the pupil lens array may have substantially the same cross-sectional shape along an entire length of the individual lenses, the pupil lens array may have a hexagonal unit cell on both sides. The hexagonal shape may be advantageous since such a shape is a relatively close fit to a circle (i.e., a hexagon resembles a circle, e.g., so that the first far field pattern shape closely matches the illumination pupil shape), and individual lenses of the pupil lens array having a cross-sectional hexagonal shape can be close-packed together.

Figure 2:
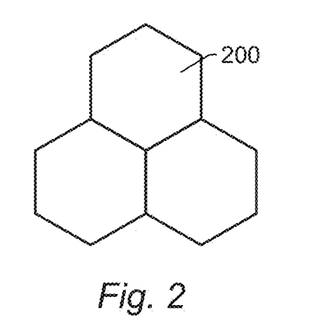
FIG. 2 is a schematic diagram illustrating a cross-sectional view of one embodiment of at least a portion of a pupil lens array.

In one such embodiment, as shown in FIG. 2, at least a portion of a pupil lens array may include three individual lenses 200, each having a cross-sectional shape that is hexagonal. In addition, as shown in FIG. 2, since each of the individual lenses has the same cross-sectional shape, they can be close-packed together in that the sides of each of the individual lenses are in contact with the sides of adjacent lenses with substantially no space in between each of the individual lenses. Although three individual lenses of the pupil lens array are shown in FIG. 2, it is to be understood that the pupil lens array may include any suitable number of individual lenses.

Figure 3:
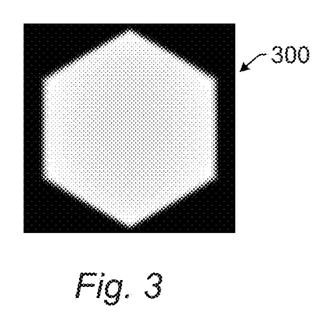
FIG. 3 is a cross-sectional view of one embodiment of a first far field pattern of light that may be generated by an embodiment of the pupil lens array.

Such a pupil lens array may be configured to produce first far field pattern of light 300 shown in FIG. 3 also having a hexagonal cross-sectional shape. In other words, FIG. 3 shows an irradiance pattern of light 300 at the front of the field lens array described further herein, where the first far field pattern of the light may be focused to by a first lens group, also referred to herein as "an additional lens group." White and light portions of the irradiance pattern correspond to illuminated areas of the irradiance pattern while black portions of the irradiance pattern correspond to non-illuminated areas of the irradiance pattern.

In one embodiment, the system includes an additional lens group or "first lens group" 106. In one such embodiment, the pupil lens array is positioned at front focal plane 108 of the additional lens group, and the additional lens group is configured to focus the first far field pattern to back focal plane 110 of the additional lens group. In this manner, the first lens group may follow the pupil lens array and may focus the substantially uniform hexagonal far field pattern of the pupil lens array to the front of the field lens array. The term "substantially uniform," as used herein is intended to mean uniform, with possibly some negligible non-uniformity due to the normal and usual limitations of physical systems. In this manner, the term "substantially uniform" is intended to encompass an exactly uniform condition as well as uniformity to the degree that the physical limitations of the system allow. Other usages herein of the term "substantially" are intended to have similar meanings.

Referring back to FIG. 1, the system further includes field lens array 112 positioned between the one or more pupil lenses and aperture stop 114 positioned proximate to the field lens array. In one embodiment, the field lens array is positioned at back focal plane 110 of the first lens group. The field lens array is configured to generate a second far field pattern of the light having a cross-sectional shape that is substantially the same as a cross-sectional shape of each individual lens in the field lens array. The system aperture stop can be separated by a relatively small distance from the field lens array to make room for the mechanical movement of the system aperture stop at the expense of slight light loss. In this manner, there may be a relatively small gap between the field lens array and the aperture stop for mechanical clearance. As such, the term "proximate" in the context of the aperture stop position with respect to the field lens array can be defined as being as close to the field lens array as possible while allowing for any mechanical movement of one or more elements of the system. The aperture stop may be configured to eliminate relatively high angle rays of light from propagating to other elements of the system, which can reduce the blurriness of the images formed by the system. The aperture stop also reduces the stray light that may degrade the signal/noise ratio and may degrade the lens mount epoxy and lens position accuracy.

The system further includes lens group 116, also referred to herein as the "second lens group." Aperture stop 114 is placed between the field lens array and the lens group. In one embodiment, aperture stop 114 is positioned at front focal plane 118 of lens group 116. For example, for telecentricity at the field plane described further herein, the aperture stop is placed at the front focal plane of the lens group. However, for the intermediate field plane, the aperture stop position can be deliberately shifted away from the front focal plane of the lens group for entire optical system optimization. In this case, the telecentricity condition is broken at the intermediate field plane. However, subsequent relay optics between the intermediate field plane and the final wafer plane can correct that, and the telecentricity condition can still be maintained at the final wafer plane.

The lens group is configured to focus the second far field pattern to back focal plane 120 of the lens group. The back focal plane of the lens group is a field plane of a wafer inspection tool at which wafer 122 is placed during wafer inspection such that the wafer is illuminated with the second far field pattern. Since the illumination pupil and the wafer under illumination are placed at the front and back focal planes of the lens group, respectively, the illumination pupil and wafer form a Fourier transform pair.

In one embodiment, the cross-sectional shape of the second far field pattern is rectangular. For example, the second far field pattern of the field lens array is the same as the field lens array's unit cell shape, which may be rectangular. In addition, since the individual lenses of the field lens array have substantially the same cross-sectional shape along an entire length of the individual lenses, the field lens array may have a rectangular unit cell on both sides. For telecentric lens array design, the front and back surfaces of individual lenslets are designed to be exactly the same in every aspect. This kind of design conserves etendue and minimizes the transmission light loss.

Figure 4:
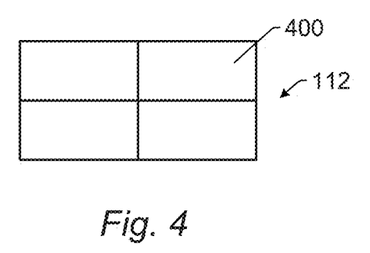
FIG. 4 is a schematic diagram illustrating a cross-sectional view of one embodiment of at least a portion of a field lens array configured as described herein.

The rectangular shape may be advantageous since individual lenses of the field lens array having a cross-sectional rectangular shape can be close-packed together. In one such embodiment, as shown in FIG. 4, at least a portion of field lens array 112 may include four individual lenses 400, each having across-sectional shape that is rectangular. In addition, as shown in FIG. 4, since each of the individual lenses has the same cross-sectional shape, they can be close-packed together in that the sides of each of the individual lenses are in contact with the sides of adjacent lenses with substantially no space in between each of the individual lenses. Although four individual lenses of the field lens array are shown in FIG. 4, it is to be understood that the field lens array may include any suitable number of individual lenses.

Figure 5:
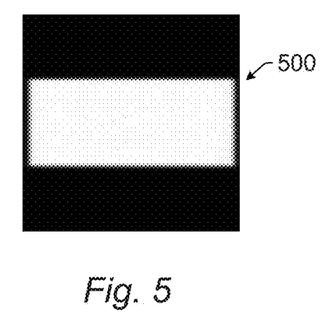
FIG. 5 is a cross-sectional view of one embodiment of a second far field pattern of light that may be generated by an embodiment of the field lens array.

Such a field lens array may be configured to produce second far field pattern of light 500 shown in FIG. 5 also having a rectangular cross-sectional shape. In other words, FIG. 5 shows an irradiance pattern of light 500 at the field stop plane/back focal plane of the lens group. White and light portions of the irradiance pattern correspond to illuminated areas of the irradiance pattern while black portions of the irradiance pattern correspond to non-illuminated areas of the irradiance pattern. In this manner, the lens group follows the field lens array/system aperture stop and focuses the rectangular far field pattern of the field lens array to the back focal plane of the lens group, which is the system field plane.

In another embodiment, the cross-sectional shape of the second far field pattern is substantially the same as a cross-sectional shape of a photosensitive area of a detector of the wafer inspection tool. For example, a detector such as a time delay integration (TDI) sensor described further herein may have a photosensitive area having a cross-sectional shape that is substantially the same as the cross-sectional shape of the far field pattern shown in FIG. 5. In this manner, the illuminated field on the wafer (the area illuminated by the second far field pattern generated by the field lens array and focused to the wafer plane by the lens group) may have the same cross-sectional shape as the photosensitive area of a detector of the wafer inspection tool, which may aid in maximizing the amount of light from the wafer that can be detected by the detector. The term "cross-sectional shape" as used herein with respect to the photosensitive area of a detector is defined as a shape of the photosensitive area in a plane perpendicular to the direction of light travel to the photosensitive area of the detector.

In this manner, the system configured to provide illumination for wafer inspection described herein may be configured as an all lens array illuminator with a pupil lens array having one unit cell shape (e.g., hexagonal) and a field lens array with a different unit cell shape (e.g., rectangular). The unit cell shape of the pupil lens array may be selected based on the desired shape of the illumination in the illumination pupil, which may be selected to enhance the defect signal/noise ratio for defects to be detected on the wafer while the unit cell shape of the field lens array may be selected to generate substantially uniform illumination field irradiance having a shape that closely matches the shape of the photosensitive area of the detector(s). For example, the pupil lens array unit cell can have any shape that can be manufactured and/or any shape that can be closely packed together (for efficiency only) such as triangular, rectangular, and hexagonal. However, the illumination pupil is in general a circular aperture. Therefore, to improve the pupil transmission efficiency, a hexagonal shape may be chosen for the pupil lens array unit cell as it closely matches the circular aperture with minimum excess area. In a similar manner, the field lens array unit cell can be anything that can be closely packed together such as triangular, rectangular, and hexagonal. However, the system detector(s) described further herein is/are in general rectangular in shape. Therefore, to improve the field transmission efficiency, a rectangular shape is generally chosen as it matches the detector geometry with minimum excess area.

The illumination pupil can also be larger or smaller than the imaging pupil. In some instances, the systems described herein may be configured such that the illumination pupil size substantially matches the imaging pupil size. As substantially high energy photons emitted front light sources such as those described further herein can cause damage to the lens mount, which is typically UV cured epoxy, it may be desirable to have the illumination pupil relatively well-defined to reduce the lens diameter (to reduce cost) and protect the lens mount area.

Figure 6:
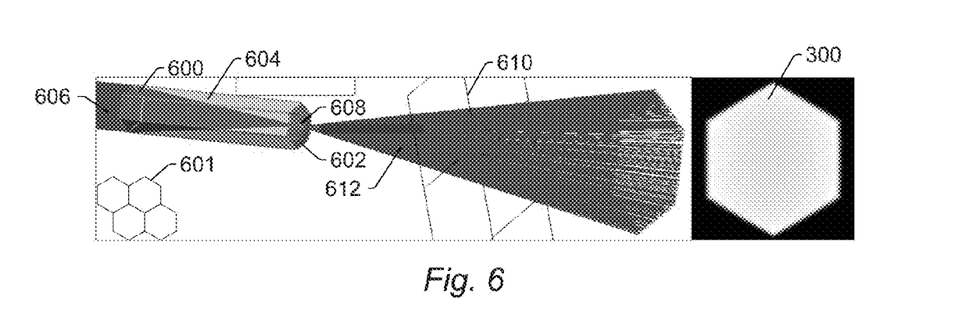
FIG. 6 is a schematic diagram illustrating a cross-sectional view of one embodiment of at least a portion of a pupil lens array, a perspective view of one embodiment of one individual lens in the pupil lens array, light rays entering, passing through, and exiting the one individual lens, and a first far field pattern of light that may be generated by the pupil lens array.
Figure 7:
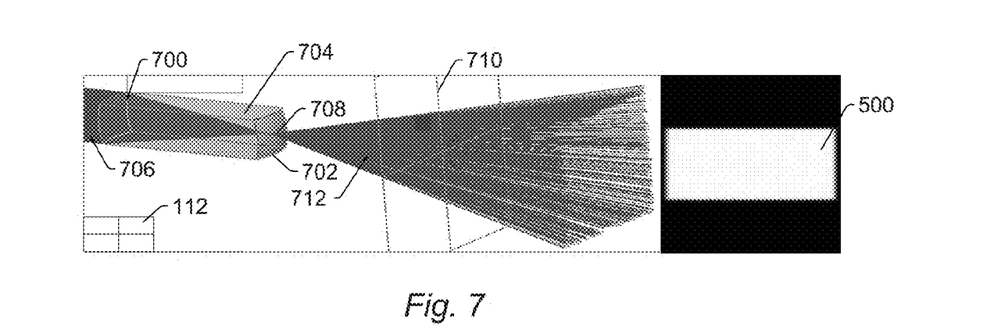
FIG. 7 is a schematic diagram illustrating a cross-sectional view of one embodiment of at least a portion of a field lens array, a perspective view of one embodiment of one individual lens in the field lens array, light rays entering, passing through, and exiting the one individual lens, and a second far field pattern of light that may be generated by the field lens array.

FIGS. 6 and 7 illustrate additional details of the pupil lens array and field lens array, respectively. For example, FIG. 6 illustrates one embodiment of a pupil lens array with a hexagonal unit cell shape and a hexagonal far field pattern. In this example, pupil lens array 601 includes a unit cell array in which each unit cell has a hexagonal shape. Although four individual lenses of the pupil lens array are shown in FIG. 6, it is to be understood that the pupil lens array may include a different number of individual lenses than that shown in FIG. 6. The pupil lens array may be further configured as described herein.

In one embodiment, the pupil lens array includes front and back surfaces that form a pair of fast Fourier transform (FFT) planes, the front surface is a front focal plane of the pupil lens array, and the back surface is a back focal plane of the pupil lens array. For example, as shown in FIG. 6, the pupil lens array may be designed such that front surface 600 and back surface 602 of each individual lens array element 604 in the pupil lens array form a pair of FFT transform planes. Therefore, the front and back surfaces of the pupil lens array will form a pair of FFT transform planes. As such, front surface 600 is the front focal plane of the individual lens array element, and back surface 602 is the back focal plane of the individual lens array element.

In another embodiment, the pupil lens array and the additional lens group are configured to generate substantially uniform illumination in an illumination pupil of the system, and the illumination pupil is located at the front focal plane of the lens group. In this manner, the illumination pupil is located at front focal plane 118 of lens group 116, as shown in FIG. 1. In general, the front focal plane, where there may be a circular aperture (e.g., aperture stop 114) that defines the maximum angle of incidence at the sample plane is referred to as the "illumination pupil." The illumination in the illumination pupil may be substantially uniform in irradiance and any other characteristics within substantially an entire area of the illumination.

In an additional embodiment, the pupil lens array is configured to focus a far field pattern of the light from the light source to a back surface of each individual lens in the pupil lens array. For example, as shown in FIG. 6, a far field pattern of incoming energy 606 from the light source (not shown in FIG. 6) such as a lamp is focused by the pupil lens array to back surface 602 of each of the individual lens array elements.

In a further embodiment, a near field pattern of the light for a back surface of each individual lens in the pupil lens array is a far field pattern of the light from the light source. For example, as shown in FIG. 6, near field pattern 608 for each of the lens array element back surfaces 602 is the far field pattern of incoming light 606 from the light source. The far field pattern for each source point of the back surface of the lens array element is the same shaped pattern (e.g., hexagonal) as determined by the pupil lens array unit cell shape. For example, if far field detector 610 is placed to detect the far field pattern for a source point of the back surface of the lens array element shown in FIG. 6, light 612 will have irradiance pattern 300 described further above. As described further above, the pupil lens array may be positioned at the front focal plane of the additional lens group. Therefore, once a lens of the additional lens group is placed with respect to the pupil lens array such that the pupil lens array is located at the front focal plane of the lens of the additional lens group, the far field pattern shown in FIG. 6 will be focused to the back focal plane of the additional lens group.

In another embodiment, the pupil lens array has a telecentric design that minimizes angular spread between far field patterns from secondary source points at a back surface of the pupil lens array thereby maximizing uniformity and irradiance of the first far field pattern. In other words, the telecentric design of the pupil lens array minimizes the angular spread between all these hexagonal far field patterns from the secondary source points at the back of the pupil lens array so that the superimposed hexagonal pattern is maximized in both uniformity and irradiance. In this manner, the pupil lens array may be configured to generate the substantially uniform illumination as described further above.

In some embodiments, a back focal plane of the pupil lens array is located at the front focal plane of the additional lens group such that individual far field patterns from the individual lenses in the pupil lens array having top hat-shaped irradiance profiles are superimposed on each other and focused to the back focal plane of the additional lens group to form illumination of the field lens array having a top hat-shaped irradiance profile. In other words, as the back focal plane of the pupil lens array is located at the front focal plane of the additional lens group, the superimposed top hat far field pattern from the pupil lens array is focused to the back focal plane of the additional lens group to form a top hat hexagonal irradiance pattern for illumination of the field lens array.

Figure 8:
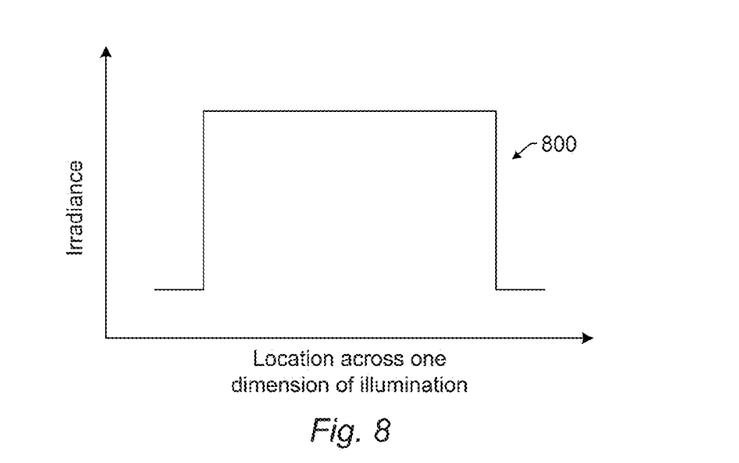
FIG. 8 is a plot showing a top hat-shaped irradiance profile.

A "top hat-shaped irradiance profile" is illustrated FIG. 8. As shown in FIG. 8, if the irradiance of light in a pattern of light is plotted as a function of location across one dimension of the illumination (e.g., location across a diameter of a cross-sectional area of the illumination, i.e., the area in a plane perpendicular to the optical axis of the illumination optics), the irradiance will generally be a rectangular function of location where locations outside of the illuminated area have a substantially low (almost no or negligible) irradiance while locations inside of the illuminated area have much higher irradiance that is substantially uniform. Such a plot is shown in FIG. 8 as plot 800 having a generally top hat shape. As such, the plot shown in FIG. 8 is an irradiance profile of light across a dimension of an illuminated area that has a top hat shape. In this manner, the top hat-shaped irradiance profiles of the light described herein have substantially uniform irradiance within the illuminated area with dramatic drop offs in irradiance at the edges of the illuminated area.

FIG. 7 illustrates one embodiment of a field lens array with a rectangular unit cell shape and a rectangular far field pattern. In this example, field lens array 112 includes a unit cell array in which each unit cell has a rectangular shape. Although four individual lenses of the field lens array are shown in FIG. 7, it is to be understood that the field lens array may include a different number of individual lenses than that shown in FIG. 7. The field lens array may be further configured as described herein.

In one embodiment, the second far field pattern focused to the back focal plane of the lens group is spatially uniform illumination. For example, the second far field pattern focused by the lens group to the back focal plane of the lens group may be uniform (or substantially uniform) in irradiance and possibly one or more other characteristics of the light across the far field pattern (and therefore in space). Generating such a far field pattern at the back focal plane of the lens group (and therefore at the field plane of the system) is important for providing substantially uniform irradiance illumination of the wafer to ensure that all locations on the wafer are inspected with substantially uniform illumination and therefore substantially uniform sensitivity.

In another embodiment, the light directed to the back focal plane of the lens group has an incident energy from all angles at which the light is directed to the back focal plane of the lens group that is substantially uniform. In other words, the light directed to the back focal plane of the lens group and therefore the field plane of the system may be consistent angularly uniform illumination in which the incident energy to the wafer from all angles within the limits of the system) is uniform or substantially uniform for all locations of the wafer. The lens group is capable of producing consistent angularly uniform illumination at the field plane due to the configurations of the field lens array and lens group described herein as well as due to the substantially uniform irradiance at the illumination pupil produced by the one or more pupil lenses (and optionally the additional lens group) described herein.

In an additional embodiment, the field lens array includes front and back surfaces that form a pair of FFT planes, the front surface is a front focal plane of the field lens array, and the back surface is a back focal plane of the field lens array. For example, as shown in FIG. 7, the field lens array may be designed such that front surface 700 and back surface 702 of each individual lens array element 704 in the field lens array form a pair of FFT transform planes. Therefore, the front and back surfaces of the field lens array will form a pair of FFT transform planes. As such, front surface 700 is the front focal plane of the individual lens array element, and back surface 702 is the back focal plane of the individual lens array element.

The far field of incoming energy 706 (e.g., from the additional lens group) is focused by the field lens array to back surface 702 of each of the individual lens array elements. Near field pattern 708 for each of the lens array element back surfaces 702 is the far field pattern of incoming light 706 (e.g., from the additional lens group). The far field pattern for each source point of the back surface of the lens array element is the same shaped pattern (e.g., rectangular) as determined by the field lens array unit cell shape. For example, if far field detector 710 is placed to detect the far field pattern for a source point of the back surface of the lens array element shown in FIG. 7, light 712 will have irradiance pattern 500 described further above. As described further above, the field lens array is positioned at the front focal plane of the lens group. Therefore, once a lens of the lens group is placed with respect to the field lens array such that the field lens array is located at the front focal plane of the lens of the lens group, the far field pattern shown in FIG. 7 will be focused to the back focal plane of the lens group.

In some embodiments, the first far field pattern focused by the additional lens group to the back focal plane of the additional lens group has a top hat-shaped irradiance profile with a first cross-sectional shape, the second far field pattern focused by the lens group to the back focal plane of the lens group has a top hat-shaped irradiance profile with a second cross-sectional shape, and the first and second cross-sectional shapes are different from each other (or can be the same). For example, as described further herein, the system may include two lens arrays (pupil lens array 601 and field lens array 112) and two sets of relay optics (additional lens group 106 and lens group 116) that together form an irradiance top hat illumination pupil with a cross-sectional shape that may be hexagonal and an irradiance top hat illumination field with a cross-sectional shape that may be rectangular.

Although the lens groups are shown in FIG. 1 as including certain types of refractive lenses, the lens groups may include any number of any suitable lenses known in the art in any suitable arrangement. For example, the lenses included in the lens groups may include spherical or aspherical lenses, with concave, convex, or flat surfaces, the surfaces of the lenses through which light passes may include a mixture of concave, convex, or flat surfaces, etc. In addition, although all of the elements (except for the system aperture) of the system are shown in FIG. 1 as refractive optical elements, the system may also include other types of optical elements (e.g., reflective, diffractive, etc.). For example, for narrow band applications, refractive optics (such as lens arrays, aspherical lenses, etc.), diffractive optics (such as computer generated holograms (CGH)), and reflective optics (micro-electro-mechanical systems (MEMS) arrays can be used. As for broad band applications, refractive and reflective beam shaping optics are preferred to reduce the impact of color.

Although the one or more pupil lenses are described above as being configured as a pupil lens array, the one or more pupil lenses do not necessarily have to include an array of lenses. For example, in one embodiment, one or more pupil lenses 104 include only one aspheric lens having only a single unit cell. In particular, the one or more pupil lenses may be a single cell aspheric lens for certain beam shaping purposes. In some such embodiments, the shape of the first far field pattern is a top hat-shaped irradiance profile. In this manner, the shape generated by the one or more pupil lenses may be a shape of a plot of irradiance of the light across one or two dimensions of the far field pattern perpendicular to the direction of travel of the light to the far field pattern. For example, such beam shaping purposes may include changing a laser Gaussian beam shape to a rectangular top hat shape. Therefore, the shape of the first far field pattern of light generated by the one or more pupil lenses may be a shape of an irradiance profile of light across the first far field pattern. In this case, the unit cell can be any shape and the lens lateral shape may not have anything to do with the far field pattern shape that it generates.

When the one or more pupil lenses do not include a pupil lens array, the system may or may not include the additional lens group described above. For example, in the aspheric configuration of the one or more pupil lenses described above, the first lens group may not be needed, and the front and back surfaces of the aspheric lens may not be a Fourier transform pair. In one embodiment in which the system does not include the additional lens group, the field lens array is positioned at a back focal plane of the one or more pupil lenses. In this case, the field lens array may be placed at a plane where the desired pupil pattern is formed by the pupil lens group, not necessarily a focal plane of the pupil lens. In a different embodiment, the system includes additional lens group 106. The one or more pupil lenses are positioned at front focal plane 108 of additional lens group 106. The additional lens group is configured to focus the first far field pattern to back focal plane 110 of the additional lens group. Field lens array 112 is positioned at the back focal plane of the additional lens group. In this manner, the additional lens group may relay the far field pattern of light generated by the one or more pupil lenses to the back focal plane of the additional lens group. The additional lens group may be further configured as described herein.

The systems configured to provide illumination described herein may also include one or more other optical elements (not shown) such as spectral filter(s), polarizing element(s), reflective element(s), spatial filter(s), beam splitter(s) and the like. Such other optical elements may be positioned in any suitable location within the system and along the path of the light through the system. In addition, although the system is shown in FIG. 1 as directing the light to the field plane at a normal or substantially normal angle of incidence, the system may be configured to direct the light to the field plane at any other suitable angle of incidence (e.g., 0 degrees to 64 degrees).

In one embodiment, the wafer inspection tool is configured for bright field (BF) inspection of the wafer. For example, the wafer inspection tool may be configured to detect light specularly reflected from the wafer and to detect defects on the wafer based on output generated by one or more detectors that is responsive to the light specularly reflected from the wafer and detected by the one or more detectors. In another embodiment, the wafer inspection toot is configured for dark field (DF) inspection of the wafer. For example, the wafer inspection tool may be configured to detect light scattered from the wafer and to detect defects on the wafer based on output generated by one or more detectors that is responsive to the light scattered from the wafer and detected by the one or more detectors. Such wafer inspection tools may be further configured as described herein.

The embodiments described herein have a number of advantages over the currently used systems for illumination of a wafer. For example, the power density of the embodiments described herein is lower than the current methods. In particular, the power density at the one or more pupil lenses may be about the same as the current method. However, the power density at the field lens array may be at least an order of magnitude lower than that at the rod used to generate a top hat field in the currently used systems and methods. In this manner, the embodiments described herein do not need a relatively long glass rod for field homogenization, which is extremely difficult to make under relatively high power density for relatively long life times for 190 nm to 260 nm wavelength bands or below. In addition, the pupil uniformity is improved over the current methods, Another embodiment relates to a system configured to inspect a wafer. Such system is also referred to herein as a "wafer inspection tool." FIG. 1 illustrates one embodiment of such a system. For example, this system includes light source 100, one or more pupil lenses 104, field lens array 112, aperture stop 114, and lens group 116, all of which may be configured as described further herein.

The system also includes one or more detectors configured to detect light from the wafer due to illumination of the wafer with the second far field pattern focused by the lens group to the field plane and to generate output responsive to the detected light. In one such embodiment, as shown in FIG. 1, the system may include detector 124 configured to detect light scattered (i.e., light not specularly reflected) from the wafer due to illumination by the system. Detector 124 may include a TDI camera, a charge coupled device (CCD) camera, or any other suitable detector known in the art. The system may also or alternatively include detector 126, which is configured to detect light specularly reflected from the wafer due to illumination by the system. For example, light specularly reflected from the wafer may be directed by beam splitter 128 to detector 126. The beam splitter may include any suitable beam splitter known in the art. Detector 126 may include any of the detectors described above. In certain tools, the same optical path and detector (e.g., detector 126) can be used for specularly reflected light as well as non-specularly reflected light. For example, the system may be configured such that the bright part in the illumination pupil is dark in the imaging (collection) pupil plane such that specularly reflected light is blocked.

The system may therefore include one or more detectors, one or more for detecting scattered light from the wafer and/or one or more for detecting specularly reflected light from the wafer. In this manner, the system may be configured for BF and/or DF inspection of the wafer. If the system includes one or more detectors for detecting scattered light from the wafer, the one or more detectors may be configured to detect light scattered at the same or different scattering angles (e.g., different polar and/or azimuthal angles). In addition, the system may include one or more optical components (not shown) positioned in the path of the light from the wafer to the detectors. Such optical components may include, for example, aperture(s), spatial filter(s), spectral filter(s), polarizing component(s), and the like.

The system also includes a computer subsystem configured to detect defects on the wafer based on the output. For example, as shown in FIG. 1, the system includes computer subsystem 130. Computer subsystem 130 is configured to acquire the output generated by detector(s) of the system. For example, output generated by the detector(s) during illumination of the wafer may be provided to computer subsystem 130. In particular, the computer subsystem may be coupled to each of the detector(s) (e.g., by one or more transmission media shown by the dashed lines in FIG. 1, which may include any suitable transmission media known in the art) such that the computer subsystem may receive the output generated by the detector(s). The computer subsystem may be coupled to each of the detectors in any other suitable manner.

The computer subsystem may be configured to detect defects on the wafer in any suitable manner. For example, the computer subsystem may be configured to apply a defect detection method and/or algorithm to the output to detect defects on the wafer. In one such example, the computer subsystem may compare the output to a threshold. Any of the output having values above the threshold may be determined to be defects while any of the output having values below the threshold may be determined to not be defects. Any other suitable defect detection method and/or algorithm may be used to detect the defects on the wafer.

The computer subsystem may also be configured for storing results of the defect detection in a computer-readable storage medium. The results may include any of the results generated by the defect detection method and/or algorithm and may be stored in any manner known in the art. The storage medium may include any suitable storage medium known in the art. After the results have been stored, the results can be accessed in the storage medium and used as described herein, formatted for display to a user, used by another software module, method, or system, etc.

Computer subsystem 130 may take various forms, including a personal computer system, mainframe computer system, workstation, system computer, image computer, programmable image computer, parallel processor, or any other device known in the art. In general, the term "computer subsystem" may be broadly defined to encompass any device having one or more processors, which executes instructions from a memory medium.

The system shown in FIG. 1 may also include stage 132 on which the wafer may be disposed during inspection. The stage may include any suitable stage known in the art. In addition, the stage may be coupled to (or part of) a robotic and/or mechanical assembly that is configured to move the wafer such that the light focused to the field plane by the lens group is scanned over the wafer during inspection. In this manner, different locations on the wafer can be inspected for defects during an inspection process.

Each of the system embodiments described herein may be further configured according to any other embodiment(s) described herein.

Further modifications and alternative embodiments of various aspects of the invention will be apparent to those skilled in the art in view of this description. For example, systems configured to provide illumination for wafer inspection performed by a wafer inspection tool are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following

What is claimed is:

1. A system configured to provide illumination for wafer inspection performed by a wafer inspection tool, comprising:
    a light source configured to generate light;
    one or more pupil lenses configured to generate a first far field pattern of the light having a shape different than a shape of the light generated by the light source;
    a field lens array positioned between the one or more pupil lenses and an aperture stop positioned proximate to the field lens array, wherein the field lens array is configured to generate a second far field pattern of the light having a cross-sectional shape that is substantially the same as a cross-sectional shape of each individual lens in the field lens array; and
    a lens group, wherein the aperture stop is placed between the field lens array and the lens group, wherein the lens group is configured to focus the second far field pattern to a back focal plane of the lens group, and wherein the back focal plane of the lens group is a field plane of a wafer inspection tool at which a wafer to be inspected is placed during wafer inspection such that the wafer is illuminated with the second far field pattern.

2. The system of claim 1, wherein the one or more pupil lenses comprise a pupil lens array, and wherein the shape that the first far field pattern has is a cross-sectional shape of the first far field pattern that is substantially the same as a cross-sectional shape of each individual lens in the pupil lens array.

3. The system of claim 2, wherein the cross-sectional shape of the first far field pattern of the light is hexagonal.

4. The system of claim 2, wherein the pupil lens array comprises front and back surfaces that form a pair of fast Fourier transform planes, wherein the front surface is a front focal plane of the pupil lens array, and wherein the back surface is a back focal plane of the pupil lens array.

5. The system of claim 2, wherein the pupil lens array is further configured to focus a far field pattern of the light from the light source to a back surface of said each individual lens in the pupil lens array.

6. The system of claim 2, wherein a near field pattern of the light for a back surface of said each individual lens in the pupil lens array is a far field pattern of the light from the light source.

7. The system of claim 2, wherein the pupil lens array has a telecentric design that minimizes angular spread between far field patterns from secondary source points at a back surface of the pupil lens array thereby maximizing uniformity and irradiance of the first far field pattern.

8. The system of claim 2, further comprising an additional lens group, wherein the pupil lens array is positioned at a front focal plane of the additional lens group, wherein the additional lens group is configured to focus the first far field pattern to a back focal plane of the additional lens group, and wherein the field lens array is positioned at the back focal plane of the additional lens group.

9. The system of claim 8, wherein the pupil lens array and the additional lens group are further configured to generate substantially uniform illumination in an illumination pupil of the system, and wherein the illumination pupil is located at a front focal plane of the lens group.

10. The system of claim 8, wherein a back focal plane of the pupil lens array is located at the front focal plane of the additional lens group such that individual far field patterns from the individual lenses in the pupil lens array having top hat-shaped irradiance profiles are superimposed on each other and focused to the back focal plane of the additional lens group to form illumination of the field lens array having a top hat-shaped irradiance profile.

11. The system of claim 8, wherein the first far field pattern focused by the additional lens group to the back focal plane of the additional lens group has a top hat-shaped irradiance profile with a first cross-sectional shape, wherein the second far field pattern focused by the lens group to the back focal plane of the lens group has a top hat-shaped irradiance profile with a second cross-sectional shape, and wherein the first and second cross-sectional shapes are different from each other.

12. The system of claim 1, wherein the cross-sectional shape of the second far field pattern is rectangular.

13. The system of claim 1, wherein the cross-sectional shape of the second far field pattern is substantially the same as a cross-sectional shape of a photosensitive area of a detector of the wafer inspection tool.

14. The system of claim 1, wherein the second far field pattern focused to the back focal plane of the lens group is spatially uniform illumination.

15. The system of claim 1, wherein the light directed to the back focal plane of the lens group has an incident energy from all angles at which the light is directed to the back focal plane of the lens group that is substantially uniform.

16. The system of claim 1, wherein the field lens array comprises front and back surfaces that form a pair of fast Fourier transform planes, wherein the front surface is a front focal plane of the field lens array, and wherein the back surface is a back focal plane of the field lens array.

17. The system of claim 1, wherein the light generated by the light source is broad band light.

18. The system of claim 1, wherein the light generated by the light source comprises deep ultraviolet light.

19. The system of claim 1, wherein the light generated by the light source comprises vacuum ultraviolet light.

20. The system of claim 1, wherein the wafer inspection tool is configured for bright field inspection of the wafer.

21. The system of claim 1, wherein the wafer inspection tool is configured for dark field inspection of the wafer.

22. The system of claim 1, wherein the field lens array is positioned at a back focal plane of the one or more pupil lenses.

23. The system of claim 1, further comprising an additional lens group, wherein the one or more pupil lenses are positioned at a front focal plane of the additional lens group, wherein the additional lens group is configured to focus the first far field pattern to a back focal plane of the additional lens group, and wherein the field lens array is positioned at the back focal plane of the additional lens group.

24. The system of claim 1, wherein the one or more pupil lenses comprise only one aspheric lens having only a single unit cell.

25. The system of claim 1, wherein the shape of the first far field pattern is a top hat-shaped irradiance profile.

26. A system configured to inspect a wafer, comprising:
a light source configured to generate light;
one or more pupil lenses configured to generate a first far field pattern of the light having a shape different than a shape of the light generated by the light source;
a field lens array positioned between the one or more pupil lenses and an aperture stop positioned proximate to the field lens array, wherein the field lens array is configured to generate a second far field pattern of the light having a cross-sectional shape that is substantially the same as a cross-sectional shape of each individual lens in the field lens array;
a lens group, wherein the aperture stop is placed between the field lens array and the lens group, wherein the lens group is configured to focus the second far field pattern to a back focal plane of the lens group, and wherein the back focal plane of the lens group is a field plane of the system at which a wafer to be inspected is placed during wafer inspection such that the wafer is illuminated with the second far field pattern;
one or more detectors configured to detect light from the wafer due to illumination of the wafer with the second far field pattern focused by the lens group to the field plane and to generate output responsive to the detected light; and
a computer subsystem configured to detect defects on the wafer based on the output.

* * * * *